US008736000B1

(12) United States Patent
Manginell et al.

(10) Patent No.: US 8,736,000 B1
(45) Date of Patent: May 27, 2014

(54) CAPACITIVE CHEMICAL SENSOR

(75) Inventors: Ronald P. Manginell, Albuquerque, NM (US); Matthew W. Moorman, Albuquerque, NM (US); David R. Wheeler, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1262 days.

(21) Appl. No.: 11/583,442

(22) Filed: Oct. 19, 2006

(51) Int. Cl.
*H01L 29/78* (2006.01)
(52) U.S. Cl.
USPC ..... 257/414; 257/215; 257/254; 257/E27.048
(58) Field of Classification Search
USPC ............ 257/414–415, 254, E27.048
See application file for complete search history.

(56) References Cited

U.S. PATENT DOCUMENTS

| | | | |
|---|---|---|---|
| 6,171,378 B1 | 1/2001 | Manginell et al. | |
| 6,730,212 B1 * | 5/2004 | Yamagishi et al. | 205/777.5 |
| 6,786,716 B1 * | 9/2004 | Gardner et al. | 431/268 |
| 7,422,724 B1 * | 9/2008 | Manginell et al. | 422/88 |
| 2003/0062905 A1 * | 4/2003 | Kollmer et al. | 324/534 |
| 2003/0085124 A1 * | 5/2003 | Ufer | 204/400 |
| 2004/0214447 A1 * | 10/2004 | Stasiak et al. | 438/710 |

OTHER PUBLICATIONS

U.S. Appl. No. 11/157,011, "Nanoparticle-Based Chemical Sensor," filed Jun. 20, 2005.
U.S. Appl. No. 10/903,329, "Mass-Sensitive Chemical Preconcentrator," filed Jul. 29, 2004.
Nobuhiro Miki et al, "Gas-Phase Selective Etching of Native Oxide," IEEE Transactions on Electron Devices, vol. 37, No. 1, Jan. 1990 pp. 107-115.
M. P. Siegal et al, "Nanoporous-carbon films for microsensor preconcentrators," Applied Physics Letters, 2002, vol. 80, No. 21, pp. 3940-3942.
P.A.M. van der Heide et al, "Etching of thin $SiO_2$," J.Vac.Sci. Technol. A., vol. 7, No. 3, May/Jun. 1989, pp. 1719-1723.
C. R. Helms et al, "Mechanisms of the $Hf/H_2O$ vapor phase etching of $SiO_2$," J.Vac.Sci. Technol. A., vol. 10, No. 4, Jul./Aug. 1992, pp. 806-811.

* cited by examiner

*Primary Examiner* — Elias M Ullah
(74) *Attorney, Agent, or Firm* — Martin I. Finston (57) ABSTRACT

A microfabricated capacitive chemical sensor can be used as an autonomous chemical sensor or as an analyte-sensitive chemical preconcentrator in a larger microanalytical system. The capacitive chemical sensor detects changes in sensing film dielectric properties, such as the dielectric constant, conductivity, or dimensionality. These changes result from the interaction of a target analyte with the sensing film. This capability provides a low-power, self-heating chemical sensor suitable for remote and unattended sensing applications. The capacitive chemical sensor also enables a smart, analyte-sensitive chemical preconcentrator. After sorption of the sample by the sensing film, the film can be rapidly heated to release the sample for further analysis. Therefore, the capacitive chemical sensor can optimize the sample collection time prior to release to enable the rapid and accurate analysis of analytes by a microanalytical system.

10 Claims, 9 Drawing Sheets

Section A - A

Section A - A

FIG. 9

CAPACITIVE CHEMICAL SENSOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to chemical sensing and, in particular, to a microfabricated capacitive chemical sensor that can use parallel-plate or fringing-field electrodes to measure the concentration of a chemical species in a gaseous or liquid environment by detecting the change in the dielectric properties of a chemically-sensitive dielectric material film.

BACKGROUND OF THE INVENTION

Chemical sensors are routinely used for the detection of various gases, chemicals, moisture, organic impurities, etc. in an ambient environment. Chemical sensors combine a chemically-sensitive interface, which sorbs chemical species (i.e., analytes) from the environment, with a physical transducer that provides an electrical output proportional to the amount of sorbed species. Typical microfabricated chemical sensors comprise a thin layer of a material that is sensitive to the concentration of a target chemical species present in the ambient atmosphere. For example, the interaction of a chemical species with the sensitive material layer can change the materials conductivity, dielectric constant, or effective thickness which can be transduced into an electrical output signal that is related to the concentration of the chemical in the ambient environment. Although many microfabricated chemical sensors exist for this purpose, a need remains for an autonomous, selective, and sensitive microfabricated chemical sensor that can be used in remote locations.

Portable, handheld microanalytical systems are also being developed to enable the rapid and sensitive detection of particular chemicals, including pollutants, high explosives, and chemical and biological warfare agents. Current gas-phase microanalytical systems typically comprise a gas chromatography column to separate the chemical species, or analytes, in a gas sample and a detector to identify the separated species. Such microanalytical systems can also include a chemical preconcentrator for sample collection. The chemical preconcentrator serves the important function of collecting and concentrating the chemical analytes on a sorptive material at the inlet of the microanalytical system. The chemical preconcentrator can deliver an extremely sharp sample plug to the downstream gas chromatograph by taking advantage of the rapid, efficient heating of the sorbed analytes with a low-heat capacity, low-loss microhotplate. The very narrow temporal plug improves separations, and therefore the signal-to-noise ratio and sensitivity to the particular chemical species of interest.

Previous microfabricated chemical preconcentrators have typically used a heated planar membrane suspended from a substrate as the microhotplate, wherein the sorptive material is disposed as a layer on a surface of the membrane to sorb the chemical species from a gas stream. The sorptive material thereby collects and concentrates the sample, and then the heated membrane thermally desorbs the sample in a short pulse for subsequent separation. See U.S. Pat. No. 6,171,378 to Manginell et al., which is incorporated herein by reference. Typically, samples are collected by the preconcentrator for a fixed period of time (e.g., 2 minutes) before they are released for analyte separation and identification. Collecting for a fixed time period is a fundamental shortcoming of the chemical analysis process. See U.S. patent application Ser. No. 10/903,329 to Manginell et al., filed Jul. 29, 2004, which is incorporated herein by reference. When concentrations of potential toxins are high, precious time is wasted collecting excess sample material. Furthermore, this excess material will often saturate the preconcentrator and overwhelm a detector, necessitating cleaning before further analysis can resume. Conversely, when target analyte concentrations in the sample stream are low, insufficient analyte may be collected for detection or proper identification. To avoid these problems, a smart, analyte-sensitive chemical preconcentrator that actively measures the change in the sorptive material's conductivity, dielectric constant, or effective thickness during the collection process is needed.

The present invention provides a microfabricated capacitive chemical sensor that can be used as an autonomous chemical sensor or as an analyte-sensitive chemical preconcentrator in a larger microanalytical system. The capacitive chemical sensor detects changes in the sensing film dielectric properties, such as the dielectric constant, conductivity, and dimensionality. These changes result from the interaction of a target analyte with the sensing dielectric film. This capability provides a low-power, self-heating chemical sensor suitable for remote and unattended sensing applications. The capacitive chemical sensor also enables a smart, analyte-sensitive chemical preconcentrator. After sorption of the sample by the sensing dielectric film, the film can be rapidly heated to release the sample for further analysis. Therefore, the capacitive chemical sensor can optimize the sample collection time prior to release to enable the rapid and accurate analysis of analytes by a microanalytical system.

SUMMARY OF THE INVENTION

The present invention is directed to a parallel-plate capacitive chemical sensor for detecting a chemical in a gas or liquid environment, comprising a substrate having an electrically insulating suspended membrane formed thereon; a lower electrode disposed on a surface of the suspended membrane; a chemically-sensitive dielectric film formed on the lower electrode; an upper electrode formed on the dielectric film; and means for detecting the mutual capacitance between the upper and lower electrodes, wherein the mutual capacitance detected is changed when the dielectric film absorbs the chemical from the environment. Access holes can be provided in the upper electrode to facilitate the absorption of the chemical from the environment by the dielectric film.

The present invention is further directed to a fringing-field capacitive chemical sensor for detecting a chemical in a gas or liquid environment, comprising a substrate having an electrically insulating suspended membrane formed thereon; interdigitated electrodes, comprising a periodic pattern of one or more sets of opposing in-plane microelectrodes, disposed on a surface of the suspended membrane; a chemically-sensitive dielectric film formed on the interdigitated electrodes; and means for detecting the mutual capacitance between the opposing parallel in-plane electrode fingers, wherein the mutual capacitance detected is changed when the dielectric film absorbs the chemical from the environment.

Either chemical sensor can further comprise a resistive heating element disposed on a side of the suspended membrane to control the temperature of the membrane. Typically, the substrate can be silicon and the suspended membrane can be silicon nitride. The chemically-sensitive dielectric film can be, for example, a sol-gel, oxide, polymer, nanoporous carbon, or ensemble of nanoparticles.

The chemical sensors can provide autonomous, selective, and sensitive chemical sensing for remote or unattended operation. Dielectric films can be chosen that chemically react with target analytes to produce changes in the capacitance of the sensor. Reactions can vary from simple compound formation, to etching, to selective cleaving of functional groups. Such reactions would produce similar or greater film impedance shifts when compared to simple adsorption. Further, sensor heating allows control of thermally-sensitive reaction and adsorption mechanisms. By maintaining a preselected set point temperature, preferential adsorption or reaction can be enhanced to provide for additional analyte selectivity and signal control. Additionally, heating enables the sensor to be cleaned by thermally-desorbing unwanted species. This periodic cleaning may extend the sensor's operational lifetime. The analyte/chemical film reaction/adsorption mechanism can occur independent of the system's power status or, in the case of a reaction requiring membrane heating, with extremely low-power output. For more remote or power-limited applications, the sensor could power on to perform a full impedance measurement only if interrogated by the user. In this way the sensor would act as an integrator to monitor long-term analyte concentrations while managing its energy supply.

When used as an analyte-sensitive chemical preconcentrator, the sensor can adsorb target analytes similar to a conventional chemical preconcentrator, but the electrodes enable interrogation of the dielectric film to determine the relative amount of adsorbed species, as well as their type. The advantages of this capability include optimized or reduced total-system analysis time, assurance that analyte concentrations are within the system detector's linear regime, and protection of the system detector from analyte overloading. Therefore, such a preconcentrator can cue the microanalytical system when the film's capacitance shift reaches desired levels and the analytes can be desorbed from the film by a rapid, high-temperature thermal pulse. In this way the microanalytical system can be optimized for performance or for rapid analysis time.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
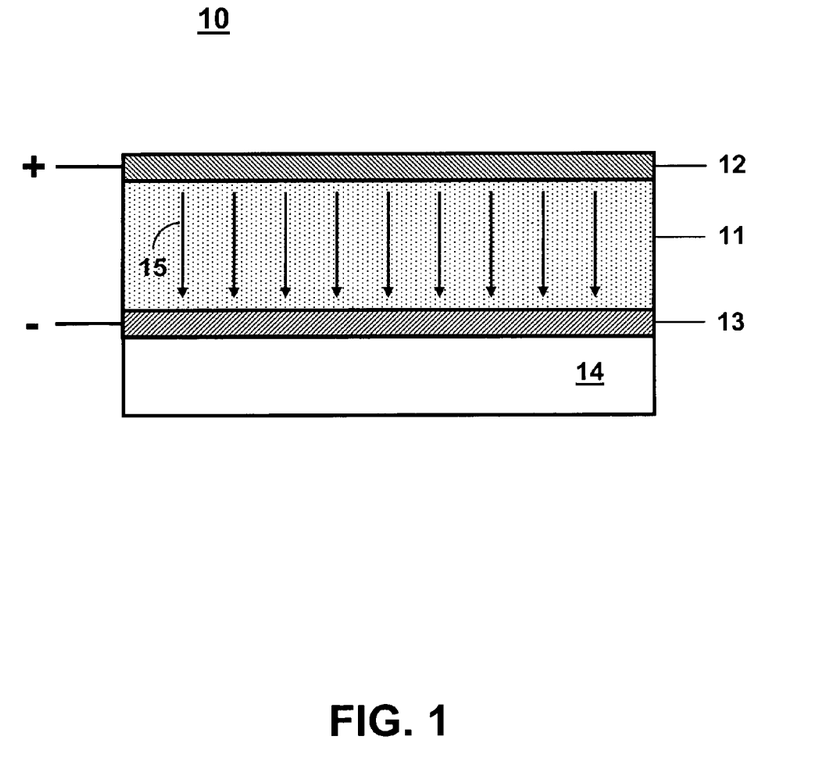
FIG. 1 shows a conceptual illustration of a parallel-plate capacitive sensor comprising a dielectric material sandwiched between opposing parallel-plate electrodes disposed on an electrically insulating substrate.

In FIG. 1 is shown a conceptual illustration of a parallel-plate capacitive sensor 10 comprising a dielectric material 11 sandwiched between opposing parallel-plate electrodes 12 and 13 disposed on an electrically insulating substrate 14. A voltage source (not shown) is connected to the driving electrode 12 and the sensing electrode 13 is connected to the input of an impedance measuring circuit (not shown). Field lines 15 go from the positive electrode 12 to the negative electrode 13. Oscillating signals from an alternating-current voltage source can be input to the driving electrode 12 to establish an alternating electric field between the driving and sensing electrodes 12 and 13. The sensing electrode 13 detects the mutual capacitance between the two electrodes 12 and 13. The mutual capacitance C of a parallel-plate capacitor is given by:

$$C = \kappa \in_o A/d$$

where A is the area of the plates, d is the distance between the plates, $\in_o$ is the permittivity constant, and $\kappa$ is the dielectric constant of the material between the plates. When used as a sensor 10, changes in the mutual capacitance can be related to changes in the dielectric constant $\kappa$ of the dielectric material 11. In turn, changes to the dielectric constant can be induced by changes in the physical, chemical, or structural properties of the dielectric material 11.

Figure 2A:
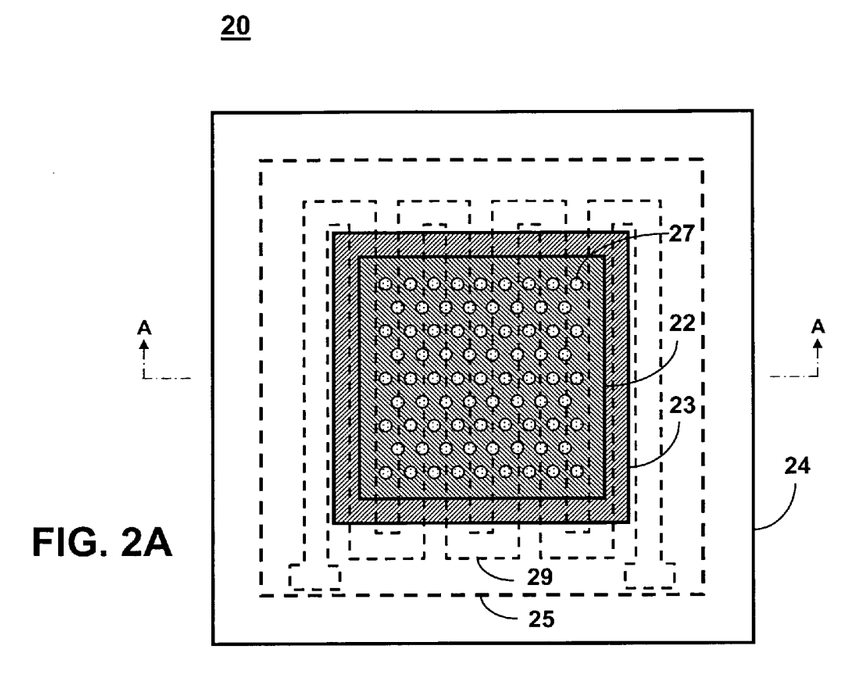
FIG. 2A shows a top-view schematic illustration of a millimeter-sized parallel-plate capacitive chemical sensor.
Figure 2B:
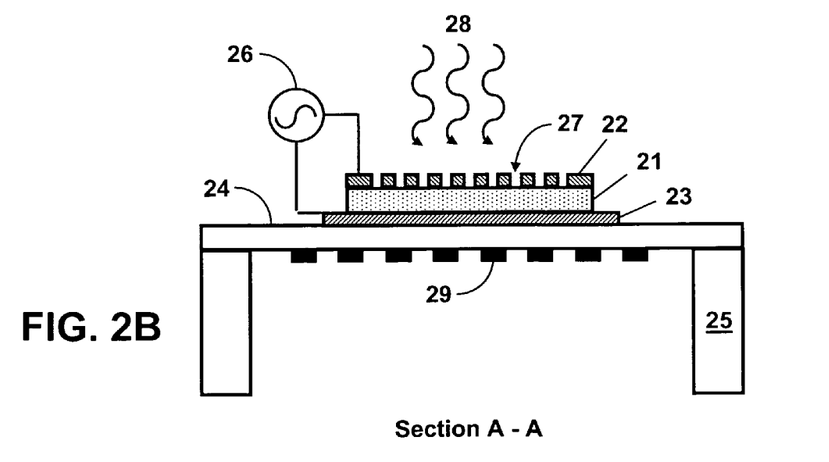
FIG. 2B shows a side-view schematic illustration of the parallel-plate capacitive chemical sensor.

In FIG. 2A is shown a top-view schematic illustration of a millimeter-sized parallel-plate capacitive chemical sensor 20 that can be fabricated using techniques known to the semiconductor integrated circuit (IC) and microelectromechanical systems (MEMS) industries. In FIG. 2B is shown a side-view schematic illustration of the chemical sensor 20. The chemical sensor 20 comprises a biologically- or chemically-sensitive dielectric material 21 sandwiched between opposing parallel-plate electrodes 22 and 23 disposed on an electrically insulating thin membrane 24. The membrane 24 is suspended from a substrate 25. The lower electrode 23 can be an electrically conducting thin film deposited on the membrane 24. The dielectric material 21 can be a thin film deposited or otherwise coated on the lower electrode 23. The upper electrode 22 can be an electrically conducting thin film deposited on the dielectric thin film 21. An alternating-current voltage source 26 can be connected between the upper electrode 22 and the lower electrode 23. The electrodes 22 and 23 can be connected to an impedance measuring circuit (not shown) to detect the mutual capacitance between the two electrodes 22 and 23. In particular, chemically-induced changes in the dielectric properties of the thin film material 21, and therefore changes in the mutual capacitance, can be detected. The upper electrode 22 can further comprise a plurality of access holes 27 to facilitate the interaction of the dielectric material 21 with gas, liquid, or chemicals from the environment 28 to be sensed. The chemical sensor 20 can further comprise a resistive heating element 29 disposed on a side of the membrane 24. As shown, the resistive heating element 29 can comprise a circuitous metal trace disposed on the side of the membrane opposite the dielectric thin film 21. The resistive heating element 29 can maintain the membrane 24 at a constant temperature when current is provided by an electrical power source. The thin membrane 24 thermally and physically isolates the resistive heating element 29 and parallel-plate electrodes 22 and 23 from the substrate 25 and the electrical power and voltage sources. Electrical contact to the resistive heating element 29 and the electrodes 22 and 23 can be established with perimeter bond pads (not shown).

Figure 3:
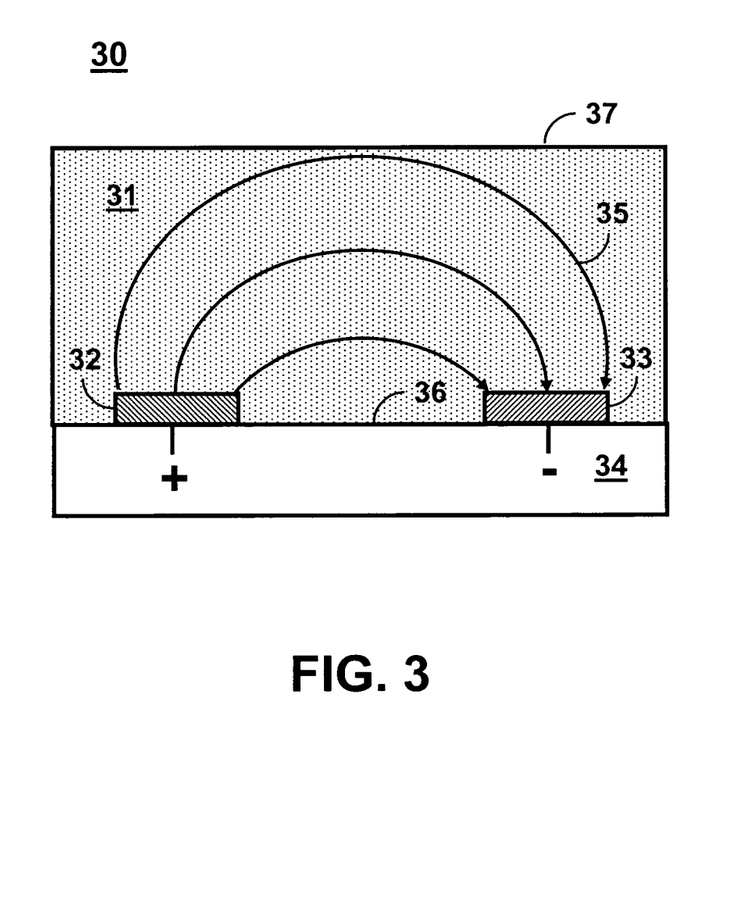
FIG. 3 shows a conceptual illustration of a fringing-field capacitive sensor comprising a dielectric film disposed on coplanar electrodes disposed on an electrically insulating substrate.

In FIG. 3 is shown a conceptual illustration of a fringing-field capacitive sensor 30 comprising a dielectric film 31 disposed on coplanar electrodes 32 and 33 disposed on an electrically insulating substrate 34. A voltage source (not shown) is connected to the driving electrode 32 and the sensing electrode 33 is connected to the input of an impedance measuring circuit (not shown). A fringing electric field penetrates into the dielectric film 31. Curved field lines 35 go from the positive electrode 32 to the negative electrode 33. The penetration depth is proportional to the distance between the driving and sensing electrodes 32 and 33. In particular, changes in the dielectric constant of the film 31 closest to the surface 36 of the electrodes has the greatest effect on the field distribution. Oscillating signals from an alternating-current voltage source can be input to the driving electrode 32 to establish an alternating fringing electric field between the electrodes 32 and 33.

An advantage of the fringing-field sensor 30 is that only single-sided access to the film 31 is required, leaving the other side 37 exposed to the environment to be sensed. Changing the dielectric properties of the material 31 changes the mutual capacitance between the electrodes 32 and 33. The change in dielectric properties can result from a change in the geometry or structure of the film, and/or a change in the dielectric constant of the film material itself. These changes can include changes in the thickness, density, structure, temperature, chemical composition, or moisture content of the film. For example, the thinning of a high-dielectric-constant film 31 reduces the effective dielectric constant of the material above the electrodes 32 and 33, thereby decreasing the mutual capacitance between the electrodes 32 and 33. The output electrode 33 detects the mutual capacitance between the two electrodes 32 and 33. A signal which represents the change in the mutual capacitance is input to the impedance measuring circuit, which can provide an output voltage that is related to the change in the dielectric properties of the film 31.

Figure 4A:
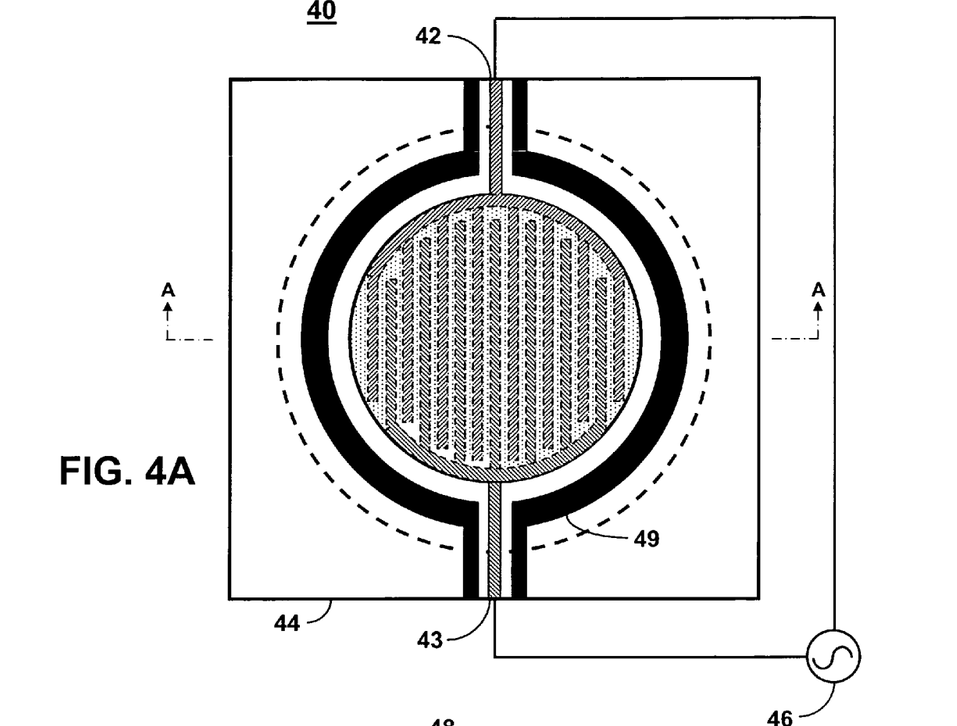
FIG. 4A shows a top-view schematic illustration of a millimeter-sized fringing-field capacitive chemical sensor.
Figure 4B:
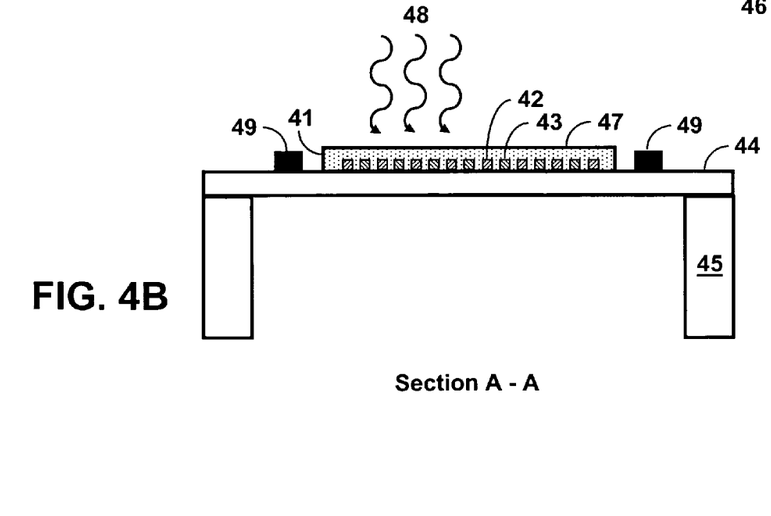
FIG. 4B shows a side-view schematic illustration of the fringing-field capacitive chemical sensor.

In FIG. 4A is shown a top-view schematic illustration of a millimeter-sized fringing-field capacitive chemical sensor 40. In FIG. 4B is shown a side-view schematic illustration of the chemical sensor 40. The fringing-field capacitive chemical sensor 40 comprises a dielectric film 41 disposed on interdigitated electrodes 42 and 43 disposed on an electrically insulating membrane 44. The membrane 44 is suspended from a substrate 45. The interdigitated electrodes 42 and 43 comprise a periodic pattern of one or more sets of opposing parallel in-plane electrode fingers. Multiple opposing fingers increase the effective length and therefore build up the capacitance associated with the electric fields that penetrate into the dielectric film 41. Other electrode geometries that comprise coplanar microelectrodes and can generate fringing electric fields can also be used. For example, the interdigitated electrodes can comprise opposing concentric in-plane ring electrodes. The dielectric material 41 can be a thin film deposited or coated on the interdigitated electrodes 42 and 43. An alternating-current voltage source 46 can be connected between the electrode 42 and the opposing interdigitated electrode 43. The electrodes 42 and 43 can be connected to an impedance measuring circuit (not shown) to detect the mutual capacitance between the two electrodes 42 and 43. In particular, chemically-induced changes in the dielectric properties of the material 41 can be detected as changes in the mutual capacitance between the electrodes 42 and 43. The single-sided access of the fringing-field chemical sensor 40 facilitates the interaction of gas, liquid, or chemicals from the environment 48 with the exposed side 47 of the film 41. The sensor 40 can further comprise a resistive heating element 49 disposed on a side on the membrane 44. The thin membrane 44 thermally and physically isolates the resistive heating element 29 and the interdigitated electrodes 42 and 43 from the substrate 45. As shown, the resistive heating element 49 can comprise a circular metal trace disposed around the periphery of a circular dielectric film 41. The resistive heating element 49 can maintain the dielectric film 41 at a constant temperature. The circular heater geometry confines the high thermal gradients to the outer edges of the membrane 44, and creates a fairly uniform temperature across the interdigitated electrodes 42 and 43. The power requirements for temperature control using this heater geometry are very low.

Fabrication of the Capacitive Chemical Sensor

A capacitive chemical sensor can be formed by a fabrication method similar to that for the chemical preconcentrator disclosed in U.S. Pat. No. 6,171,378. The processing steps include material deposition, photolithography, masking, etching, mask stripping and cleaning and are generally well-known in the IC and MEMS industries. The fabrication of the parallel-plate capacitive chemical sensor 20 comprises the steps of forming a suspended membrane 24 on a substrate 25, forming a lower electrode 23 on the membrane 24, forming a chemically-sensitive dielectric thin film 21 on the lower electrode 23, and forming an upper electrode 22 on the dielectric thin film 21. Access holes 27 can further be formed in the upper electrode 22. The fabrication of the fringing-field capacitive chemical sensor 40 comprises the steps of forming a suspended membrane 44 on a substrate 45, forming interdigitated electrodes 42 and 43 on the suspended membrane 44, and forming a chemically-sensitive dielectric film 41 on the interdigitated electrodes 42 and 43. For either sensor 20 or 40, a resistive heating element 29 or 49 can further be formed on either side of the suspended membrane 24 or 44.

The substrate generally comprises a semiconductor (e.g., silicon or gallium arsenide) or a dielectric (e.g., a glass, quartz, fused silica, a plastic, or a ceramic), with a thickness generally about 400-500 µm. The step of forming the suspended membrane comprises depositing a film on the surface of the substrate and removing material from the substrate underneath a portion of the deposited film. This removal can be done using either anisotropic wet etching (e.g., with potassium hydroxide) or by reactive ion etching, or by a combination of both types of etching. The suspended membrane is typically formed as a rectangle or polygon with lateral dimensions from about one to a few millimeters on a side (e.g., a square of 1-3 mm on a side), or alternatively as a circle or ellipse with a size from one to a few millimeters. The suspended membrane is supported at its edges by attachment to the substrate. The membrane can be sufficiently thick (generally about 0.5-1 µm total thickness) for robustness as required for handling and to support the electrodes, dielectric material, and resistive heating element. Additionally, the membrane can be sufficiently robust to withstand any stress induced by a mismatch in thermal expansion coefficients of the membrane and the supporting substrate upon heating to a constant temperature. Low-pressure chemically vapor deposited silicon nitride is a preferred membrane material due to its low stress, low thermal conductivity, low heat capacity, and compatibility with IC processing steps. The low thermal conductivity minimizes heat loss to the substrate. Other materials such as polycrystalline silicon, silicon oxynitride, and silicon carbide can also be used to form the membrane.

Prior to release, thin-film parallel-plate or interdigitated electrodes can be patterned on the suspended membrane using e-beam evaporation. Various metals or doped semiconductors can be used for the electrodes. The interdigitated electrodes can be made relatively thick to allow easy charge migration along the electrodes and to increase the effective capacitance. For example, the finger thickness and electrode spacing of the interdigitated electrodes can range from a few to tens of microns. For example, the electrodes can typically comprise about 5000 Å of Au with a 100 Å Cr adhesion layer patterned on the membrane.

By applying a chemically-sensitive dielectric film over the membrane, analytes of interest can be selectively adsorbed from gasses flowing over the device. The types of sensing dielectric films and their characteristics can vary based on the intended application. Sensing films are preferably thermally stable, electrically insulating, and low stress. While electrically conducting films can be used, such films would require insulation layers between the electrodes and the film to prevent electrical shorting. The stress state of the film is preferably sufficiently low during application and use that the structural integrity of the suspended membrane is not compromised. The thickness of such dielectric films is generally on the scale of several thousand angstroms. Extremely thin films will not be adequately sampled by the electrical fringing field, while thicker films may isolate the chemical-dielectric material interface from interrogation by the electrical fringing field.

Films can be deposited through a variety of techniques such as sputtering, vapor deposition, spray coating, drop coating, or self-assembling chemistries. Appropriate dielectric films for deposition comprise polymers, porous sol-gels, oxides, nanoporous-carbon (NPC), and nanoparticles. The use of polymers, sol-gels, or oxides for selective coatings is well known to those having skill in the art. NPC coatings can be deposited using a pulsed-laser deposition process. These films are nanocrystalline to amorphous forms of graphite and have extremely high surface area and an affinity for a wide variety of chemical compounds. NPC is chemically inert, has no-to-low stress, and is thermally stable to over 600° C. See M. P. Siegal et al., *Appl. Phys. Lett.* 80, 3940 (2002), which is incorporated herein by reference.

Nanoparticle films are another suitable film material. First, a small ensemble of nanoparticles can be assembled between microelectrodes. Once the particles are in place, the ensemble of nanoparticles can be stabilized using surfactant (capping agent) replacement and crosslinking methodology. With this methodology, the capping agents on a nanoparticle are completely or partially substituted with other tighter binding ligands. Once the ensemble is crosslinked the sensor can be used in both liquid and gas sensing applications. To increase the sensitivity of the ensemble, the crosslinking ligands can be π-conjugated molecules with an analyte specific binding group or chemistry. By employing π-conjugated molecules to bridge the nanoparticles, the interparticle conduction mechanism can be dominated by the bridging ligand, provided the remaining capping agent molecules are nonconductive and the orbitals of the bridging ligand are energetically favorable for influencing electron transfer. Binding of an analyte molecule to one of the bridging ligands will change its charge transport properties. This change in charge transport can be measured electrically and an analyte concentration can be determined. The mechanism of impedance change is based on changes in the organic bridging molecules; this is fundamentally different than currently employed swelling mechanisms. Additionally, if there is a specific electrical response (perhaps a specific impedance change at a characteristic frequency or a distinctive current-voltage or IV curve) then there exists a built in verification or analyte identity check. The sensitivity of the sensor can be tuned by controlling the extent of the percolation path generated during the crosslinking step. A limited number of percolation paths would increase the sensitivity of the sensor, while an ensemble of particles with a large number of paths would respond a wider range of analyte concentrations before saturating. Employing multiple identically functionalized sensors, but with different numbers of nanoparticles or nanoparticles crosslinking units, can improve the analyte discrimination and concentration determination and redundancy. See U.S. patent application Ser. No. 11/157,011 to Wheeler et al., filed Jun. 20, 2005, which is incorporated herein by reference.

The resistive heating element generally can comprise one or more circular or circuitous metal traces formed from one or more layers of deposited metals including platinum, molybdenum, titanium, chromium, palladium, gold, and tungsten that can be patterned on either side of the membrane. An optional temperature sensor can be located on the membrane proximate to the resistive heating element to aid in controlling and measuring the temperature of the dielectric thin film.

The chemical sensor can further comprise low-power, signal-processing and signal-amplifying CMOS. Integrating CMOS on a silicon substrate increases sensor sensitivity and provides an extremely low-level impedance measurement of analytes.

Use of a Fringing-Field Capacitive Chemical Sensor for the Detection of Hydrogen Fluoride An example that illustrates the chemical sensor's versatility and the utility of active temperature control is as a hydrogen fluoride (HF) detector. Current technology for the detection of HF vapor is inappropriate for unattended and, especially, remote deployment. In particular, current HF detectors lack the low-power requirements and small footprint necessary for unattended operation.

A fringing-field capacitive chemical sensor, of the type shown in FIGS. 4A and 4B, was used to detect elevated levels of HF in various environments. The fringing-field capacitive HF sensor comprised a set of interdigitated electrodes, a chemically-selective dielectric film deposited over the interdigitated electrodes, and a circular resistive heating element with a temperature control circuit to control humidity on the film. Silicon nitride was used as the sensor membrane material due to its low thermal conductivity, robustness, and resistance to HF attack. A KOH etching step was used to dissolve the silicon on the underside of the membrane, which released the SiN. The membrane measured approximately 2.2 mm on a side when completely released. The selective dielectric film was comprised of silicon dioxide ($SiO_2$). HF has a strong reactivity with $SiO_2$, which is the primary component of the dielectric film, and results in the removal of the $SiO_2$. The removal of this film occurs regardless of the sensor's power status, and can be measured as a shift in capacitance. The HF/SiO$_2$ reaction mechanism, however, is highly dependent on ambient humidity, and so humidity regulation by active temperature control may be required to maintain optimized sensor response. Failure to regulate humidity produces a variable reaction rate which may make it difficult to determine the correct HF concentration in an ambient environment. However, the membrane temperature needs to be regulated by only about 5-10° C. The power requirements were typically only a few tens of mW. This enables the sensor to operate in an extremely low-power integrator mode to establish the presence of HF over a long time duration. The reduced power-requirement and system size enables the chemical sensor to perform in remote environments.

A variety of different techniques were used to deposit the sensing dielectric SiO$_2$ film. These techniques included a nebulizer, an ultrasonic nozzle, a micropipette, and plasma-enhanced chemical vapor deposition (PECVD). The first three techniques were used to deposit a sol-gel, which is a suspension of SiO$_2$ particles in a solvent. As the solvent evaporates it creates a highly porous structure, not unlike glass foam. By controlling solvent concentration and evaporation, the porosity of the solid film can be controlled. The final technique, PECVD, can deposit a pure solid oxide on the sensor surface. This oxide is much denser than a sol-gel, and does not feature a high porosity. The primary advantage of the PECVD technique is the better control of oxide thickness across the wafer and between wafers.

The nebulizer sprays the film by entraining the sol-gel liquid in a pressurized stream of nitrogen or air, and a shadow mask can be used to define the film coverage over the interdigitated electrodes. The nebulizer creates a wide variation in droplet size which results in a very rough, irregular surface, and a large run-to-run variation in the film thickness. The advantage of such a film is that it provides an ample supply of nucleation sites for water condensation. The high porosity of sol-gels, as well as the oxide's affinity for moisture, causes humidity to adsorb into the film and line the pore walls. This results in moisture being trapped into the film, which can facilitate the HF etching reaction, even in low humidity environments.

The micropipette produces a film by using pressurized nitrogen or air to force a tightly controlled droplet of sol-gel through a pipette onto the sensor surface. This technique enables good volume control, but the placement of the droplet can be difficult.

Ultrasonic nozzle deposition uses ultrasonic agitation of a liquid reservoir to create precise, repeatable droplets. These droplets leave the nozzle tip with an extremely low velocity. The low velocity droplet greatly reduces overspray, which is the tendency for a droplet to splash when it hits a surface. This allows for well-defined films with more exact definition. Due to the repeatability of droplet formation and non-clogging nature of this nozzle, the film morphology and thickness appear to be more repeatable than those deposited via nebulizer.

The PECVD oxide is deposited by using a vapor, which condenses across the wafer surface. The deposition takes place between 250-350° C.; the higher the temperature the denser and less porous the film. The film thickness is primarily a function of deposition time. This enables repeatable and controllable film thickness across the interdigitated electrode surface. After the film is deposited, a photolithography step defines the oxide, and a liquid HF dip is used to precisely pattern the oxide over the interdigitated electrode. The oxide is much denser than the sol-gel, which provides an order of magnitude larger capacitance increase of the sensor. While the capacitance of sol-gel films are measured in the hundreds of femtofarads, oxide films are measured in the picofarads. The disadvantage of depositing the sensing film in this manner is the relatively low porosity when compared to a sol-gel. This lower porosity reduces the surface area available for HF to react with, and the amount of ambient moisture that can be resident in the film.

Chemistry of Hydrogen Fluoride Sensing

HF is a long-lasting compound that is one of the most stable forms of fluorine in the atmosphere. HF is a caustic gas that is known to have deleterious health affects on humans. HF tends to form a fog and sink to ground level due to its higher density than air. It also readily mixes with atmospheric water vapor to form hydrofluoric acid. HF detection using the fringing-field capacitive chemical sensor depends on the chemical transduction of gaseous HF to a change in capacitance of the sensor. Therefore, an understanding of the HF—SiO$_2$ reaction mechanism is important to understanding the sensor's operation. Fortunately, the basic reaction mechanism is well-documented, due to use of HF in the semiconductor industry to remove SiO$_2$ during microelectronic processing. See Nobuhiro Miki et al., "Gas-phase selective etching of native oxide", *IEEE Trans. Electron Devices* 37(1), 107 (1990); and C. R. Helms et al., "Mechanisms of the HF/H$_2$O vapor phase etching of SiO$_2$", *J. Vac. Sci. Technol. A* 10(4), 806 (1992).

Atmospheric HF reacts with the SiO$_2$ on the sensor's surface to remove the oxide, and hence produce a capacitive shift. This shift results because the dielectric constant of SiO$_2$ is approximately a factor of four larger than that of the surrounding air. There are three primary chemical reactions that govern this HF—SiO$_2$ reaction:

$$SiO_2 + 4HF \leftrightharpoons SiF_4 + 2H_2O \quad (1)$$

$$SiO_2 + 6HF \rightarrow H_2SiF_6 + 2H_2O \quad (2)$$

$$H_2SiF_6 \leftrightharpoons 2HF + SiF_4 \quad (3)$$

Reactions (1) and (3) are reversible. These reversibilities have important consequences for high humidity etching and HF recycling at the SiO$_2$ surface, respectively.

Figure 5A:
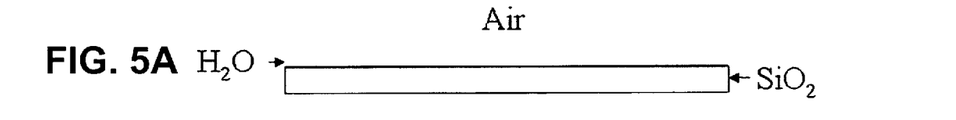
FIGS. 5A-5D show a schematic illustration of the progression of the etching behavior of a thin film of silicon dioxide after being exposed to a hydrogen fluoride atmosphere.
Figure 5B:
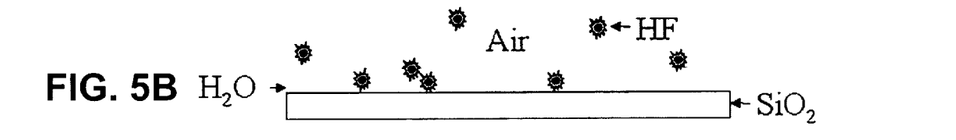
Figure 5C:
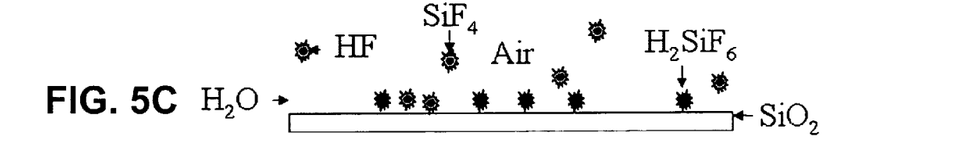
Figure 5D:
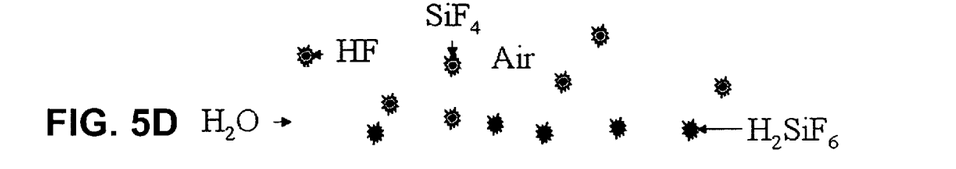

FIGS. 5A-5D show a schematic illustration of the progression of the HF—SiO$_2$ etching behavior. In FIG. 5A is shown a thin film of SiO$_2$, and a thin layer of atmospheric water that is present on an oxide surface. In FIG. 5B is shown how atmospheric HF requires this water layer to condense onto the surface, disassociate into hydrofluoric acid, and begin etching of the SiO$_2$. In FIG. 5C is shown the reaction products H$_2$SiF$_6$ and SiF$_4$ being formed, along with water, from reactions (1) and (2). H$_2$SiF$_6$ stays in the liquid phase, while SiF$_4$ tends to evolve into the vapor phase. The water formation continues to generate a medium on the surface that results in further HF disassociation, but too much water formation can disrupt the etching mechanism. By the reversible reaction (1), the water layer can trap the SiF$_4$ and encourage the reformation of oxide molecules. The liquid H$_2$SiF$_6$ is, in effect, a recycler of HF molecules. By disassociating, in reaction (3), H$_2$SiF$_6$ can efficiently reintroduce HF molecules into the liquid layer, and in this way it is possible for each HF molecule to remove more than one molecule of SiO$_2$. Additionally, the H$_2$SiF$_6$ also acts to stabilize the liquid phase in certain etching conditions. As shown in FIG. 5D, after the SiO$_2$ layer is completely etched, a liquid layer consisting of water and $H_2SiF_6$ remains on the surface. This liquid layer eventually evaporates.

Hydrogen Fluoride Sensing Experiments

A fixture of inert plastic was machined to hold the sensor while it was being exposed to HF. O-rings were used to seal the gas flow within the fixture so that only the membrane area of the device was exposed to the gas. Outside the O-ring, electrical connections for the heater and interdigitated electrodes were made using pogo pins. A gas-handling system was constructed to meter HF to the test fixture. The HF for testing came from a gas cylinder that was a custom mix of 110 ppm anhydrous HF in nitrogen. The flow of this mix was controlled via pressure regulators and needle valves. A separate gas line flowing house air was also installed as part of the system. The air was pushed through a bubbler tube to controllably humidify the air, and was metered, using a mass flow controller, into a T-junction with the HF mixture. The combined gas flow then went through the test fixture. Test points were included throughout the system to calibrate gas flow, and test the gas mixture's humidity. A temperature control circuit was used to regulate the membrane's temperature, thereby to control the water layer on the oxide coating. The circuit operated in a feedback mode that maintained the resistance, and therefore the temperature, of the sensor's heater at a user-defined set point. To make sensor measurements, a laptop computer was coupled with an impedance analyzer. Analyzer readings were performed at an AC frequency of between 300-500 kHz, and the decoupled resistance and capacitance measurements were recorded into a database, along with a time stamp of when the reading was taken. Data points were averaged 256 times, and were taken in 30 sec. to 2 min. intervals.

Initial experiments were performed with a sensor that had interdigitated electrodes coated with nebulizer-deposited sol-gel. These initial sensor experiments did not use temperature control. Typical HF concentrations in these initial experiments were on the order of 10-50 ppm, while typical total gas flows ranged from 20-30 ccm. Humidity ranges were varied widely, from almost dry air to an excess of 80% relative humidity (RH). A standard operational procedure was developed that required the sensor to sit in the gas flow for at least 24 hours before and after HF exposure to make certain the RH and gas flow stabilized, so as not to attribute a signal shift to changes in flow or humidity. Signal variation during this steady state operation, without HF, was extremely low.

Figure 6:
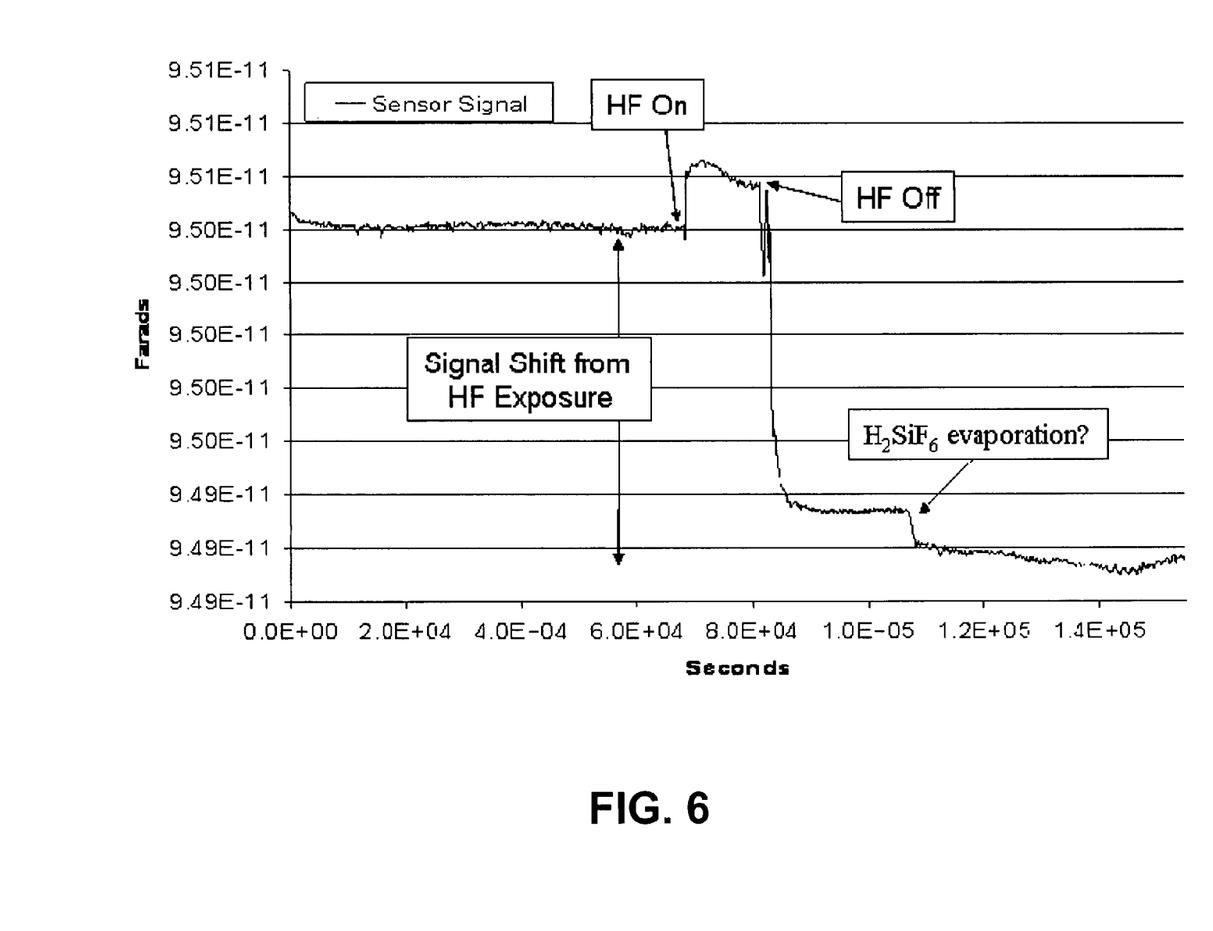
FIG. 6 shows a graph of the capacitance versus time for a fringing-field capacitive chemical sensor comprising a sol-gel dielectric film after being exposed to a hydrogen fluoride atmosphere.

In FIG. 6 is shown a graph of the capacitance versus time for this sensor after exposure to HF. The sensor under test had a 5 micron gap between interdigitated electrode fingers. The sensor was exposed to a 26 sccm gas flow with a RH of nearly 77% and 55 ppm HF. The ppm concentration represents the amount of HF in the gas phase. A capacitive shift of approximately 120 femtofarads occurred, which corresponded to complete removal of approximately 5000 Å of sol-gel film after a 3.5 hour exposure to the gas flow. This shift corresponded to an average of 24 attofarads capacitance per Å of sol-gel. Approximately 1 Å of sol-gel was removed for every 8 seconds of HF exposure. The capacitance generally decreased, as expected, indicating the gradual removal of a higher dielectric constant material ($SiO_2$) and replacement with a lower one (air). However, there was a notable increase in capacitance at etching onset. This increase was likely due to water creation during initial etching. Pure water has a relatively high dielectric constant, on the order of 78.5, due to its polar nature. Water creation during the etching process contributes to the effective dielectric constant of the sensing material. Much of the created water evaporates into the gas phase, however some of it stays resident on the sol-gel film. As the etching progresses, the removal of the sol-gel begins to reduce available locations for the water film to nucleate, and the overall capacitance begins to decrease due to the loss of dielectric material. These factors eventually overwhelm water's contribution to the effective dielectric constant, and the capacitive signal decreases. At about $1.10 \times 10^5$ seconds into the testing there was a decrease in signal after several hours of apparent baseline. The $H_2SiF_6$ reaction product stays resident primarily in the liquid phase and usually needs to be rinsed or allowed to evaporate before the surface can be considered clean. The signal decrease may mark the evaporation of this thin water and $H_2SiF_6$ layer, as illustrated in FIG. 5D.

A second set of experiments was preformed with a heated fringing-field capacitive chemical sensor. Heating of the chemically-sensitive dielectric film can drive off adsorbed water and other contaminants which might otherwise affect the capacitance measurement. Literature indicates that the HF etch rate peaks at 25° C. but decreases with increasing temperature, until it becomes very slow at over 40° C. See P. A. M. van der Heide et al., "Etching of thin $SiO_2$ layers using wet HF gas", *J. Vac. Sci. Technol. A* 7(3), 1719 (1989). This etching rate reversal is due to the elevated temperature driving off the water film on the oxide surface, and decreasing the available water for HF condensation.

Figure 7:
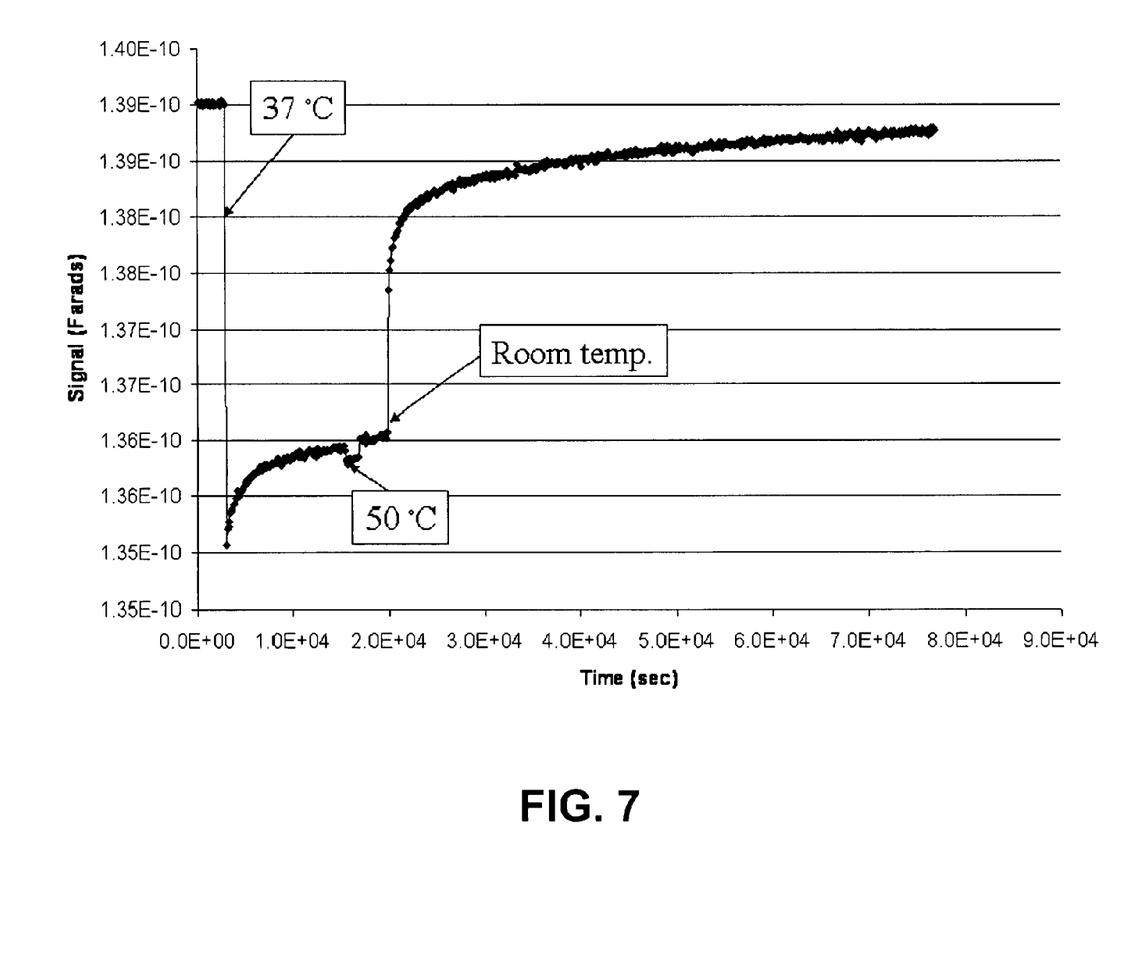
FIG. 7 shows a graph of capacitance versus time for a fringing-field capacitive chemical sensor comprising a resistive heating element following step changes in temperature.

To demonstrate the ability of a heated membrane to drive off adsorbed water, the capacitance of a device was monitored at a typical indoor RH of 45%. In FIG. 7 is shown a graph of capacitance versus time for the heated chemical sensor following step changes in temperature. The temperature was stepped from 23° C. to 37° C., then to 50° C., and then back to 23° C. The initial capacitance decrease, resulting from the temperature step from 23° C. to 37° C., was over 3 picofarads. The capacitance then asymptotically drifted upward from this value. An increase to 50° C. caused little signal change, since the majority of the water had been driven from the film. When the active heating was discontinued, the capacitance once more asymptotically climbed back to its room temperature value.

Figure 8:
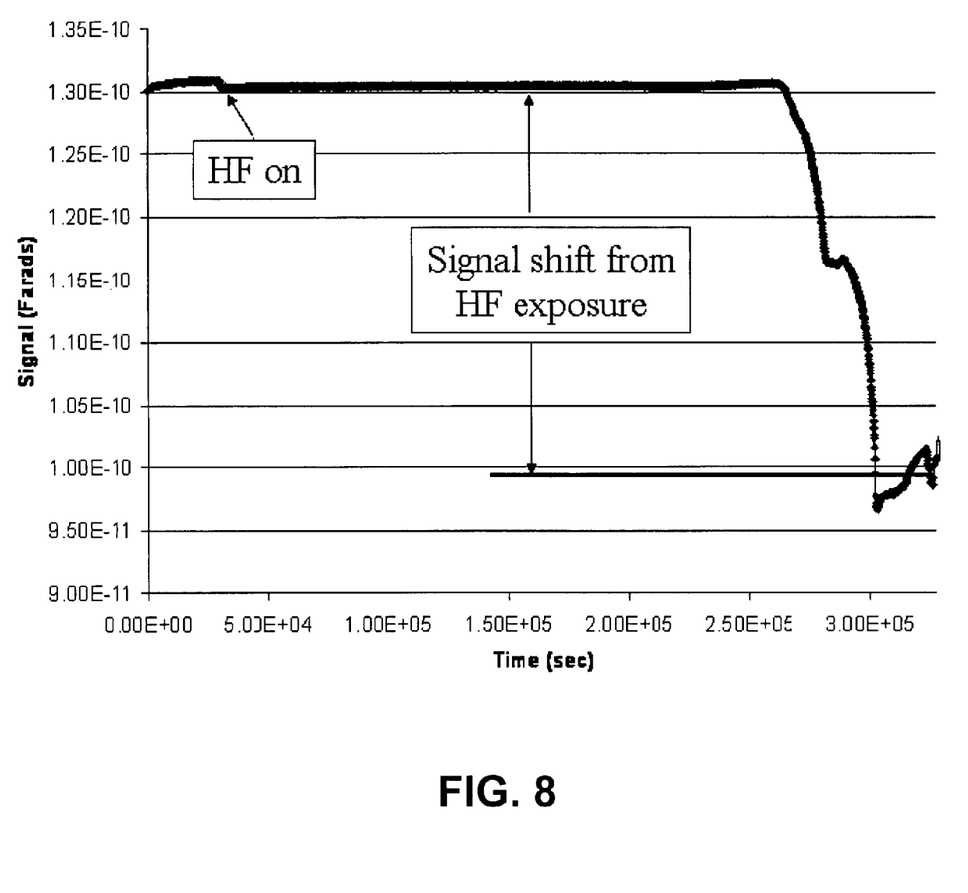
FIG. 8 shows a graph of capacitance versus time for a fringing-field capacitive chemical sensor comprising a PECVD oxide dielectric film and an interdigitated electrode with a 5 micron interelectrode gap after the sensor is heated to 36° C. and exposed to a hydrogen fluoride atmosphere.
Figure 9:
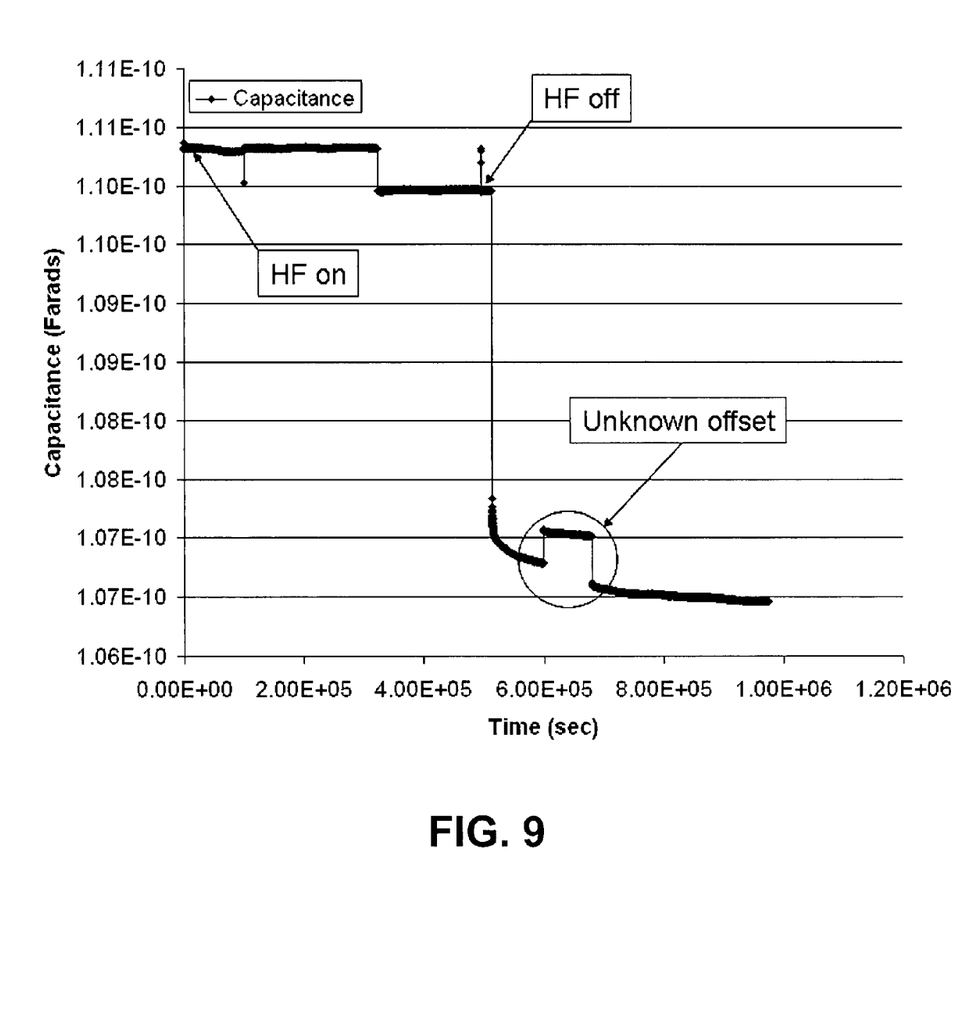
FIG. 9 shows a graph of capacitance versus time for a fringing-field capacitive chemical sensor comprising a PECVD oxide dielectric film and an interdigitated electrode with a 10 micron interelectrode gap after being exposed to a hydrogen fluoride atmosphere.

In FIGS. 8 and 9 are shown graphs of capacitance versus time for fringing-field capacitive chemical sensors, each with a PECVD oxide thickness of 4200 Å, after exposure to an environment having an HF concentration of 4 ppm. The results shown in FIG. 8 are for a sensor with a 5 micron interdigitated electrode gap and a membrane heated to 36° C. The results shown in FIG. 9 are for a sensor with a 10 micron interdigitated electrode gap and a membrane held at ambient room temperature. The differences in baseline capacitance between the two sensors primarily stem from the variation in interdigitated electrode geometry. The testing conditions were a RH of 41-45% and a total gas flow of 40 sccm. The dielectric constant of the denser PECVD oxide was much higher than the sol-gel. The total capacitance shift on the 5-micron-gap interdigitated electrode was nearly 30 picofarads, which equates to 7 femtofarads per angstrom of oxide film.

Comparing the delay between the introduction of HF and the first indication of the etching reaction in FIGS. 8 and 9 indicates that the heated sensor responded to etching 57% faster than the unheated sensor. Once the etching reaction had been initiated, the heated sensor experienced a largely continuous, though slow, etching reaction which resulted in the total removal of the oxide film. The unheated sensor experienced a partial etching reaction which partially removed the oxide very quickly, but then the reaction ceased and no change was seen for another 50 hours. Thereafter, the reaction once more initiated and quickly removed the majority of the sensing PECVD oxide film. Comparing the time necessary for complete removal of the film indicates the heated sensor etched over 400% faster.

The present invention has been described as a capacitive chemical sensor. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A fringing-field capacitive chemical sensor for detecting a chemical in a gas or liquid environment, comprising:
   a substrate having an electrically insulating suspended membrane formed thereon;
   interdigitated electrodes, comprising a periodic pattern of one or more sets of opposing in-plane microelectrodes, disposed on a surface of the suspended membrane;
   a chemically-sensitive dielectric film formed on the interdigitated electrodes;
   an alternating-current voltage source connected between the opposing in-plane microelectrodes; and
   means for detecting the mutual capacitance between the opposing in-plane microelectrodes when an alternating-current voltage is applied to the opposing in-plane microelectrodes by the voltage source, wherein the mutual capacitance detected is changed when the dielectric film absorbs the chemical from the environment.

2. The chemical sensor of claim 1, a resistive heating element disposed on a side of the suspended membrane.

3. The chemical sensor of claim 1, wherein the interdigitated electrodes comprise a periodic pattern of one or more sets of opposing parallel in-plane electrode fingers.

4. The chemical sensor of claim 3, wherein the substrate comprises silicon, gallium arsenide, glass, quartz, fused silica, plastic, or ceramic.

5. The chemical sensor of claim 1, wherein the interdigitated electrodes comprise a periodic pattern of one or more sets of opposing concentric in-plane electrode rings.

6. The chemical sensor of claim 1, wherein the substrate comprises a semiconductor or a dielectric.

7. The chemical sensor of claim 1, wherein the suspended membrane comprises silicon nitride, polycrystalline silicon, silicon oxynitride, or silicon carbide.

8. The chemical sensor of claim 1, wherein the dielectric film comprises silicon dioxide.

9. The chemical sensor of claim 1, wherein the dielectric film comprises a sol-gel or oxide.

10. The chemical sensor of claim 1, wherein the dielectric film comprises a polymer, nanoporous-carbon, or ensemble of nanoparticles.

* * * * *